(12) United States Patent
Dax et al.

(10) Patent No.: US 7,470,821 B2
(45) Date of Patent: Dec. 30, 2008

(54) ALDOLASE-INHIBITING AROMATIC COMPOUNDS

(75) Inventors: Chantal Dax, Toulouse (FR); Casimir Blonski, Ramonville (FR); Laurent Azema, Auterive (FR); Jurgen Sygusch, Montreal (CA)

(73) Assignees: Valorisation-Recherche, Limited Partnership, Montreal, Quebec (CA); Universite Paul Sabatier Toulouse III, Toulouse Cedex (FR)

(*) Notice: Subject to any disclaimer, the term of this patent is extended or adjusted under 35 U.S.C. 154(b) by 189 days.

(21) Appl. No.: 10/562,251

(22) PCT Filed: Jun. 29, 2004

(86) PCT No.: PCT/FR2004/001664

§ 371 (c)(1),
(2), (4) Date: Jun. 26, 2006

(87) PCT Pub. No.: WO2005/012313

PCT Pub. Date: Feb. 10, 2005

(65) Prior Publication Data

US 2007/0043002 A1     Feb. 22, 2007

(30) Foreign Application Priority Data

Jul. 2, 2003   (FR) .................... 03 08042

(51) Int. Cl.
C07C 47/00 (2006.01)
(52) U.S. Cl. .................... 568/420; 568/425; 568/439; 568/440; 568/441; 514/125; 514/700; 514/732
(58) Field of Classification Search ................ 568/420, 568/425, 439–441; 514/125, 700, 732
See application file for complete search history.

(56) References Cited

OTHER PUBLICATIONS

C. Blonski, D. de Moissac, J. Perie, J. Sygusch,☐☐Inhibition of rabbit muscle aldolase by phosphorylated aromatic compounds☐☐Biochem. J., 1997, 323, 71-77.*
Berthiaume et al., "Differential Usage of the Carboxyl-terminal Region among Aldolase Isozymes," *J. Biol. Chem.* 268(15):10826-10835 (1993).
Bilger et al., "Synthèse des nitro-2 naphto-[1,2-b]furannes monométhoxylés sur l'homocycle extérieur," *Eur. J. Med. Chem.* 22:363-365 (1987) (English language abstract).
Blonski et al., "Inhibition of Rabbit Muscle Aldolase by Phosphorylated Aromatic Compounds," *Biochem. J.* 323:71-77 (1997).
Farquhar et al., "Biologically Reversible Phosphate-Protective Groups," *J. Pharm. Sci.* 72(3):324-325 (1983).
Gefflaut et al., "Slow Reversible Inhibitions of Rabbit Muscle Aldolase with Substrate Analogues: Synthesis, Enzymatic Kinetics and UV Difference Spectroscopy Studies," *Bioorg. Med. Chem.* 4(12):2043-2054 (1996).
Gefflaut et al., "Class I Aldolases: Substrate Specificity, Mechanism, Inhibitors and Structural Aspects," *Prog. Biophys. Mol. Biol.* 63:301-340 (1995).
Hartman and Barker, "An Exploration of the Active Site of Aldolase Using Structural Analogs of Fructose Diphosphate," *Biochem.* 4(6):1068-1075 (1965).
Johnson et al., "Derivatives of 5-Methoxyhydrindene and 6-Methoxytetralin. Synthesis of β-(2-Carboxy-5-Methoxyphenyl)-propionic Acid," *J. Am. Chem. Soc.* 66(2):218-222 (1944).
Johnson et al., "A Plan for Distinguishing Between Some Five- and Six-membered Ring Ketones," *J. Am. Chem. Soc.* 67(10):1745-1754 (1945).
Ladame et al., "Selective Phosphorylation on Primary Alcohols of Unprotected Polyols," *Phosphorus Sulfur Silicon* 174:37-47 (2001).
Lefebvre et al., "Mononucleoside Phosphotriester Derivatives with S-Acyl-2-thioethyl Bioreversible Phosphate-Protecting Groups: Intracellular Delivery of 3'-Aziodo-2',3'-didexoxythymidine 5'-Monophosphate," *J. Med. Chem.* 38:3941-3950 (1995).
McCarty, "Prospects for Glycerol-Rescued Hypoglycemia as a Cancer Therapy," *Med. Hypotheses* 56(3):286-289 (2001).
Meloche, "Bromopyruvate Inactivation of 2-Keto-3-deoxy-6-phosphogluconic Aldolase. I. Kinetic Evidence for Active Site Specificity," *Biochem.* 6(8):2273-2280 (1967).
Morris and Tolan, "Site-directed Mutagenesis Identifies Aspartate 33 as a Previously Unidentified Critical Residue in the Catalytic Mechanism of Rabbit Aldolase A," *J. Biol. Chem.* 268(2):1095-1100 (1993).
Morrison and Walsh, "The Behavior and Significance of Slow-Binding Enzyme Inhibitors," *Adv. Enzymol. Relat. Areas Mol. Biol.* 61:201-301 (1988).
Nieschalk et al., "Synthesis of Monofluoro- and Difluoro-methylenephosphonate Analogues of *sn*-Glycerol-3-phosphate as Substrates for Glycerol-3-phosphate Dehydrogenase and the X-ray Structure of the Fluoromethylenephosphonate Moiety," *Tetrahedron* 52(1):165-176 (1996).
Page et al., "Synthesis of Phosphono Analogues of Dihydroxyacetone Phosphate and Glyceraldehyde 3-Phosphate," *Bioorg. Med. Chem.* 7:1403-1412 (1999).
Puech et al., "Intracellular Delivery of Nucleoside Monophosphates through a Reductase-Mediated Activation Process," *Antiviral Res.* 22:155-174 (1993).

(Continued)

*Primary Examiner*—Daniel M Sullivan
*Assistant Examiner*—Sudhakar Katakam
(74) *Attorney, Agent, or Firm*—Clark & Elbing LLP; Kristina Bieker-Brady (57) ABSTRACT

The invention relates to novel aldolase-inhibiting compounds that can be advantageously used as medicaments (in therapeutic doses), especially for treating certain cancers, due to the inhibition efficacy thereof. An inventive compound corresponds to general formula (I) wherein the aldehyde group (—CHO) and the phenol group (—OH) are linked to two carbon atoms adjacent to the same aromatic chain, i.e., the first aromatic chain, and R is a phosphate group or a phosphate group mimetic linked to a carbon atom of the second aromatic chain.

12 Claims, 3 Drawing Sheets

OTHER PUBLICATIONS

Rutter, "Evolution of Aldolase," *Fed. Proc.* 23:1248-1257 (1964).
Srivastva and Farquhar, "Bioreversible Phosphate Protective Groups: Synthesis and Stability of Model Acyloxymethyl Phosphates," *Bioorg. Chem.* 12:118-129 (1984).
Stowell et al., "A New Method for the Phosphorylation of Alcohols and Phenols," *Tetrahedron Lett.* 36(11):1825-1826 (1995).
Tosquellas et al., "The Pro-Oligonucleotide Approach: Solid Phase Synthesis and Preliminary Evaluation of Model Pro-Dodecathymidylates," *Nucleic Acids Res.* 26(9):2069-2074 (1998).

Communication from the European Patent Office for European Patent Application Serial No. 04767508.7 dated Nov. 14, 2006 and partial English language translation.
Communication from the European Patent Office for European Patent Application Serial No. 04767508.7 dated May 10, 2007 and partial English language translation.
Communication from the European Patent Office for European Patent Application Serial No. 04767508.7 dated Oct. 17, 2007 and partial English language translation.

* cited by examiner

FIGURE 1

Scheme 1

$$k_{app} = k_{-2} + \left[ k_2 \frac{[I]/K_i}{1 + [I]/K_i} \right] \quad \text{eqn. (1)}$$

$$[EI^*] = \frac{([E]_t + [I]_t + K_d) - \sqrt{([E]_t + [I]_t + K_d)^2 - 4[E]_t [I]_t}}{2} \quad \text{eqn. (2)}$$

$$t_{1/2} = \frac{\ln 2}{k_2} \left[ 1 + \frac{K_i}{[I]} \right] \quad \text{eqn. (3)}$$

ALDOLASE-INHIBITING AROMATIC COMPOUNDS

CROSS-REFERENCE TO RELATED APPLICATIONS

This application is the U.S. national stage application of International Application Number PCT/FR2004/001664, filed Jun. 29, 2004, which, in turn, claims the benefit of French Patent Application Serial Number 03/08042, filed Jul. 2, 2003.

The invention relates to novel glycolysis-inhibiting compounds whose action is in the form of aldolase inhibition. The invention also relates to their synthesis method and applications, particularly in the manufacture of medicaments for treating cancer.

Glycolysis is a complex mechanism involving a cascade of ten different enzymes for ensuring anaerobic conversion with release of energy stored in the form of adenosine-5-triphosphate (ATP).

Among the ten enzymes involved in glycolysis, the aldolases (fructose-1,6-bisphosphate aldolases) and homotetrameric enzymes take part in an important stage: cleavage of the fructose-1,6-bisphosphate ($Fru(1,6)P_2$) into two phosphate trioses, dihydroxyacetone phosphate (DHAP) and glyceraldehyde-3-phosphate (GAP). Splitting of the ($Fru(1,6)P_2$) by the aldolases is performed by a multi-stage mechanism whereby several clearly identified intermediate products are defined.

Aldolases are essential to the glycolysis path, and consequently valuable in pyruvate and ATP synthesis.

Aldolases fall into two classes (Ruther et al., 1964, Fred. Proc. Fed. Am. Soc. Exp. Biol., 23:1248-1257), with those of one class distinguished from those of the other in particular by their sources, though by their function mode as well. Class I aldolases, found in animal species, higher plants and certain parasites fix the ($Fru(1,6)P_2$) by forming a proton imine (or Schiff base) between a lysine residue (lys-229) in the active site and the substrate. Class II aldolases are specific to procaryote organisms. They need to have a bivalent metal ion at their catalytic site for fixing and stabilizing the substrate in the enol form prior to cleavage.

Among the currently known class I aldolase inhibiters, we can cite the competitive inhibitors, in particular those described in Blonski C. et al., 1997 (Biochem J., 323:71-77): phosphated derivatives of hydroquinone ($HQN-P_2$), resorcinol ($RSN-P_2$) and benzaldehyde-4-phosphate (HBA-P). When tested on rabbit muscle aldolase, these inhibitors demonstrate a dissociation constant (or inhibition constant) $K_i$ of around 135, 50 and 500 µM. Also known are phosphorylated compounds of inhibition constant $K_i$ in the order of 30-40 µM (Hartman, et al., 1965, Biochemistry, 4:1068-1075).

We can also cite 2-hydroxybenzaldehyde-4-phosphate (Blonski C. et al., 1997 Biochem J., 323:71-77), a reversible inhibitor that depends on the global inhibition constant time $K_i^*$ of 35±5 µM, capable of reducing 80% of aldolase activity at an inhibitor concentration of around 200 µM.

The same as these compounds, the other presently known aldolase inhibitors (Gefflaut T. et al., 1995, Prog. Biophys. Mol. Biol., 63(3):301-340), and glycolysis inhibitors in general, show weak inhibiting activity, unless used at extremely high concentrations, which considerably limits their field of application. Moreover, their application at weak concentrations, for example at concentrations compatible with therapeutic doses, can scarcely be envisaged.

A great many applications, and in particular in medicine, strive for significant glycolysis inhibition, at inhibitor concentrations weak enough to avoid any harmful effect on the patient. Accordingly, we are aware of one approach, known as the glycerol rescued hypoglycemia (GRH) approach, designed to treat certain cancers and solid tumors (McCarty M. F., 2001, Med. Hypotheses, 56:286-289), and which in particular is based on two findings.

First, it has been shown that solid tumors and lethal cancers that develop in tissues with a predominant weak oxygen concentration (hypoxia conditions) have a phenotype that causes glycolysis to act as a single path for energy production. It has also been shown that cells of this type are also characterized by the absence of glycerol kinase activity, a particular enzyme making it possible for healthy cells to use glycerol as a glucose replacement.

The GRH approach thus contemplates inhibiting the glycolysis path in all of the patient's cells, while providing a sufficient dose of glycerol by way of a single energy source. Cancer cells whose glycolysis represents the main ATP synthesis path are thus "starved" and unable to use glycose or glycerol as an alternative source of energy to glucose. As for healthy cells, owing to glycerol-kinase activity and other enzymes from the lower part of glycolysis (those of triose), they can use glycerol to synthesize pyruvate. Thus the cancer cells are starved while healthy tissues are ensured of getting enough energy.

Nevertheless, at the present no cancer treatment involving the GRH approach has yet to be undertaken owing to the absence of suitably efficient glycolysis inhibitors, and more specifically inhibitors of one of the enzymes from the top of glycolysis (those of hexoses).

By the same token, with glycolysis representing the only energy synthesis path for many parasites, glycolysis blocking could also be a very promising approach for treating many diseases of parasitic origin.

Accordingly there currently exists a real need to have at least one efficient glycolysis inhibitor available, especially with an eye toward conquering cancer as well as certain parasitic diseases, or in terms of eradicating any organism for which glycolysis is a principal, or essential, energy synthesis path.

The present invention contemplates filling in the aforementioned gaps by proposing new chemical compounds able to inhibit glycolysis, and in particular the activity of class I aldolases.

More specifically, the invention contemplates compounds that, owing to their aldolase inhibition efficacy can be used as medicaments, i.e., effectively when at therapeutic doses, in particular as part of cancer treatment.

The invention also relates to proposing applications of these compounds as glycolysis inhibitor agents, except for therapeutic applications. By extension, the invention relates to proposing new medicaments, in particular for treating cancer and/or parasitic diseases.

Lastly, the invention relates to a inventive process for synthesizing compounds, one that is simple to carry out, with sufficient quantities and inexpensive, in other words, a process compatible with the economic limitations of industrial-scale production.

The following terminology will be used throughout the document:
   aromatic chain: the conjugate cycle of an aromatic nucleus wherein free electrons can shift from one carbon atom to another without linking to either of them (delocalization of electrons due to the effect of resonance), and from one carbon atom in a chain to a carbon atom in another chain; naphthalene-type aromatic nuclei used in the present invention thus have alternating simple links (σ links) and double links (π links), resulting in a highly delocalized system of π electrons between the two aromatic chains forming these nuclei, phosphate group mimetic: replaces a chemical compound other than a phosphate group, adapted to increase the bioavailability of the chemical compound with regard to its protein target (aldolase) in accordance with the invention; phosphate group mimetics can be of two types: enzymolabile protecting groups or stable phosphate analogues, enzymolabile protecting group: a phosphate group mimetic adapted to allow passive diffusion of the compound through cell or parasite membrane systems, according to one method for masking charges, consequently, within the cell or parasite, undergoing an enzymatic transformation (or deprotection) so that it can generate a phosphate group or a stable phosphate analogue.

stable phosphate analogue: a phosphate group mimetic that, in comparison to a phosphate group, shows greater stability vis-à-vis physiological conditions, in particular pH and/or the enzymatic environment.

The invention relates to an aromatic compound comprising an aldehyde group, a phenol group and a phosphate group or a phosphate group mimetic, such as an enzymolabile protecting group or a stable phosphate analogue, wherein:

its aromatic nucleus is formed by condensation of two aromatic benzene chains, it corresponds to the following general formula:

wherein:
the aldehyde group (—CHO) and the phenol group (—OH) are linked to two adjacent carbon atoms from the same aromatic chain i.e., the first aromatic chain, and R is a phosphate group or a phosphate group mimetic linked to a carbon atom of a second aromatic chain, i.e., the second aromatic chain.

Although the actual class I aldolase inhibition mechanisms are not definitively elucidated by each compound of the invention, the inventors' work on certain ones of them, as well as the modeling of the active site of the various class I aldolases, makes it possible to foresee an efficient inhibition of these aldolases inasmuch as the compounds meet the above definition.

Accordingly, the invention makes it possible to see that the simultaneous presence of a phosphate group, a hydroxyl group and an aldehyde group, grafted onto a plane-geometry structure such as an aromatic naphthalene nucleus, is necessary in order to generate good recognition and an appreciable affinity with the active aldolase site.

The phosphate group is essential to recognition of the inhibitor by aldolase. The phosphate group fits into the enzyme recognition pocket, thereby making it possible for the aromatic compound to become properly oriented inside the active site. The aromatic compound then exposes the aldehyde and phenol groups at a considerable distance from at least one of the three lysine residues (Lys-107, Lys-146, Lys-229) from the active site so as to form, along with this site and at a physiological pH, a stable protonated imine or Schiff-base link. The requirement that the phosphate group be arranged in an aromatic chain other than the one occupied by aldehyde and hydroxyl is therefore highly important. In fact, an aromatic naphthalene nucleus makes it possible to position the hydroxyl and aldehyde at a distance from the phosphate group, particularly appropriate for satisfactory affinity between the compound and the aldolases. The distance separating the phosphate group from the aldehyde and hydroxyl group leads to recognition of the phosphate group by the aldolases and stabilization of the compound in the active site, by means of one of the three lysine residues, with very few constraints placed on the compound, thus little energy expenditure.

On the other hand, the respective positions of the aldehyde and hydroxyl with regard to the phosphate play an important role in the selectivity of a particular aldolase for a well defined compound in accordance with the invention.

Lastly, the presence of the hydroxyl and aldehyde groups on two carbon atoms adjacent to the same aromatic chain is essential and governs the formation of this particular link on the class I aldolase active site. The hydroxyl group likely plays the role of acid catalyst during dehydration of the intermediary carbinolamine, then likely participates in stabilizing the proton Schiff base, thereby generating an effective and virtually irreversible, if not irreversible, inhibition.

An aromatic naphthalene nucleus onto which phosphate, aldehyde and phenol groups have been grafted in specific positions also and advantageously makes it possible to define a plane-geometry compound with a more constrained conformation than with aldolase substrates (Fru(1,6)P$_2$), GAP, DHAP), whose dimensions are adapted to the accessibility constraints of the compound on the aldolase active site as well as to the steric hindrance at this level.

Such aromatic compounds are therefore capable of occupying the class I aldolase active site so that fructose-1,6-bisphosphate linking and cleavage can be prevented, and lastly, leading to blocking of glycolysis. Such aromatic compounds are thus capable of efficiently inhibiting the aldolases of eucaryote and/or parasite cells, therefore blocking glycolysis of eucaryote and/or parasite cells.

However, whenever intracellular and/or intraparasitic inhibition is desired, the ionizing state of the phosphate group, required for recognition and covalent attachment of a compound according to the invention at the aldolase active site, creates a problem for passing these inhibitors through the cell membrane, leading to poor bioavailability of these compounds or weak overall activity.

An initial approach making it possible to improve the bioavailability of a phosphate compound consists of protecting the phosphate groups so as to mask these charges temporarily—in particular by means of enzymolabile protecting groups—and thus make their passage through the cell membranes possible in a passive sense.

Moreover, pH, especially in living, cell and parasite tissues, could be the cause of spontaneous cleavage of the phosphate group. By the same token, many enzymes—in particular phosphatases—are capable of cleaving the aromatic-phosphate cycle link. In addition, for applications to tissues, cells and living parasites, it is preferable to replace these phosphate groups with mimetics, especially with stable phosphate analogues.

Advantageously, a phosphate group mimetic is selected from among:

an enzymolabile protecting group adapted to allow said aromatic compound to pass through cell and/or parasite membrane systems passively and, once inside a cell or parasite, to be able to form a phosphate group or a stable analogue of a phosphate group, a stable phosphate analogue adapted to protect the aromatic compound from spontaneous and/or enzymatic dephosphorylation, in particular for cell and/or parasite phosphatase.

By way of example, without limitation, of compounds in accordance with the invention that are able to inhibit aldolases, we can cite compounds that, based on official nomenclature, can be designated as 5-formyl-6-hydroxy-2-naphthylphosphate, 6-formyl-5-hydroxy-2-naphthylphosphate, 4-formyl-5-hydroxy-1-naphthylphosphate, 5-formyl-4-hydroxy-1-naphthylphosphate, 4-formyl-3-hydroxy-2-naphthylphosphate, 3-formyl-4-hydroxy-2-naphthylphosphate, 3-formyl-2-hydroxy-1-naphthylphosphate, 2-formyl-3-hydroxy-1-naphthylphosphate, or a derivative of the latter obtained by substituting the phosphate group by a phosphate group mimetic in accordance with the invention.

Advantageously, an aromatic compound in accordance with the invention has the general formula:

(II)

where $R_1$ is a phosphate group or a phosphate group mimetic.

Whenever $R_1$ is a phosphate group, the aromatic compound in accordance with the general formula (II) is, based on the official nomenclature, then designated as 5-formyl-6-hydroxy-2-naphthylphosphate (referred to herein as FHN-P). Moreover, a compound in accordance with the invention and of general formula (II) can be 5-formyl-6-hydroxy-2-naphthylphosphate or a derivative thereof, obtained by substituting the phosphate group by a phosphate group mimetic in accordance with the invention.

Studies of FHN-P interaction with class I aldolases, more particularly with rabbit muscle aldolase, were carried out using UV-visible differential spectroscopy. At the same time, these studies were completed by enzymatic kinetic analyses and experiments using mutated aldolases.

Using the rabbit muscle aldolase, the invention made it possible to demonstrate the formation of a Schiff base between the aldehyde group of the aromatic compound in accordance with the invention and the enzyme. This also made it possible to show that Lys-107 residue is involved in the formation of this Schiff base. Lastly, inhibition of rabbit muscle aldolase by FHN-P was defined as a time-dependent reversible inhibition (slow-binding inhibition). This type of inhibition, other than showing a high degree of selectivity, is characterized by a slow binding of the inhibitor to the enzyme, which can be as efficient as inhibition caused by a chemically reactive irreversible inhibitor (Morrison and Walsch, 1988. Adv. Enzymol. Relat. Aeras Mol. Biol., 61:201-301). Inhibition of rabbit muscle aldolase by FHN-P is characterized by a global inhibition constant $K_i^*$ of some 25 nM. Therefore at the present this compound represents the most powerful reversible slow-binding inhibitor with regard to class I aldolases. And going further, as with any inhibition involving the formation of a Schiff base between the inhibitor and a lysine residue, this inhibition can be made irreversible by treating the inhibitor-enzyme complex with sodium borohydride.

It should be noted that for aldolase inhibition, a compound such as 2-(4-formyl-3-hydroxyphenyl)-1-ethylene dihydrogene phosphate can be considered as an equivalent of FHN-P. In effect, this compound responds—in a manner quite comparable to FHN-P—to the conditions required for the aldolase inhibition contemplated above. The presence of the phosphate group of this compound first of all makes recognition by the aldolases possible. Exactly like FHN-P, this compound is then oriented inside the active site, and bearing in mind the distance separating the phosphate group from the aldehyde and phenol groups, which are very noticeably identical to that of the FHN-P groups, it exposes its aldehyde and phenol groups to one of the neighboring lysine residues.

Advantageously, an enzymolabile protecting group in accordance with the invention is a group that tends to be deprotected by one or more intracellular esterases.

Advantageously and in accordance with the invention, this enzymolabile protecting group has the following general formula:

(III)

where R' can be selected from among one of the following groups:

(IV)

(V)

An aromatic compound in accordance with the invention thus has an enzymolabile protecting group, of a type known as an oxymethylester. The deprotection mechanisms of such an enzymolabile group have in particular been described by Farquhar et al., 1983 (J. Pharm. Sci., 72:324-325), and by Srivastva et al., 1984 (Bioorg. Chem., 12:118-124).

Advantageously, based on another variant, an enzymolabile protecting group in accordance with the invention that can be deprotected by intracellular esterases has the following general formula:

(VI)

where R″ can be selected from among one of the following groups:

Although the thioester enzymolabile protecting groups use the same enzymes as do oxymethylester enzymolabile protecting groups for their protection, the reactive mechanism is nonetheless quite different, and has in particular been described by Lefebvre et al., 1995 (J. Med. Chem., 38:3941-3950).

Based on one variant regarding the temporary masking of the charge, an enzymolabile protecting group in accordance with the invention can be deprotected by one or more intracellular reductases.

Advantageously, based on this variant, an enzymolabile protecting group has the following general formula:

where R‴ can be selected from among one of the following groups:

The deprotection mechanisms of such an enzymolabile protecting group have been described by Puech et al., 1993 (Antiviral Res., 22:155-174).

It is of course possible to compensate for the ionized state of the phosphate group of certain aromatic compounds in accordance with the invention using techniques other than masking of charges by enzymolabile protecting groups. In accordance with the application contemplated (for aldolases whether or not extracted from cells), one might prefer to resort to a particular encapsulation (gallenical type) or to a particular administration technique (injection methods), supplementing or substituting the enzymolabile protecting groups, in particular the aforementioned one.

Advantageously, a stable phosphate analogue in accordance with the invention can be selected from among one of the following groups:
methylenephosphonate
difluoromethylenephosphonate
monofluoromethylenephosphonate in particular as described in Nieschalk J. et al., 1996 (Tetrahedron Lett., 52(1):165-176).

Advantageously and in accordance with the invention, a hydrogen atom from at least one carbon atom from at least one of the aromatic chains is substituted by a substituent, said hydrophobic substituent adapted to improve the global hydrophobicity of the compound. The presence of such a group facilitates access of an aromatic compound in accordance with the invention to the active and relatively hydrophobic aldolase site. It is further recommended that a group compatible with synthesis of the compound in accordance with the invention be selected, and that consideration be given to the limitations of steric hindrance at the aldolase active site.

Advantageously, each hydrophobic substituent in accordance with the invention is a principal chain alkyl group with at least three carbon atoms.

The invention also contemplates an aromatic compound in accordance with the invention to be used as an agent for inhibiting class I aldolase activity, and by extrapolation, as a glycolysis inhibiting agent in eucaryote organisms. Advantageously, an aromatic compound is not used for therapy.

Advantageously and in accordance with the invention, an aromatic compound used for this purpose could have an aldolase inhibition constant $K_i$ of less than 25 μM, in particular less than 50 nM and typically around 25 nM.

Advantageously and in accordance with the invention, an aromatic compound used for this purpose could inhibit at least one aldolase, irreversibly or virtually irreversibly.

The invention also contemplates a process for inhibiting extracellular or intracellular aldolases, advantageously with the exception of intracellular aldolases from non-isolated living cells of a human body, animal body or human embryo, in which these aldolases are placed in contact with at least one aromatic compound in accordance with the invention, at least in sufficient quantity to create a notable effect on aldolase activity.

Advantageously, one process in accordance with the invention is applied to cell glycolysis inhibition.

Advantageously, one process in accordance with the invention can be applied to curb development of a cancer cell.

The invention also contemplates a medicament comprising an aromatic compound in accordance with the invention.

In the fight against cancer, various therapeutic approaches have been contemplated (chemotherapy, radiotherapy, surgery, etc.) and many treatments are currently being used. However, there is presently no totally effective cancer treatment. The choice of treatments nowadays is generally based on the type of tissue and organs affected, as well as on the degree of spreading and the malignity thereof. Nevertheless, patients cannot endure many more-or-less long-term treatments. Accordingly, a multi-therapy approach is generally prescribed, thus the need for a variety of treatments for dealing with the same cancer and which can be prescribed as an alternate for a patient. The possibility of applying the GRH approach could lead to new treatments, and thus a major advance in the fight against cancer. An aromatic compound in accordance with the invention makes it possible to apply the GRH approach very favorably.

The invention also contemplates use of an aromatic compound in accordance with the invention to manufacture a medicament for cancer treatment, in particular for manufacturing a medicament for treating cancer by means of the GRH approach.

The invention also contemplates a method for synthesizing an aromatic compound in accordance with the invention.

In one aspect of the invention, the method allows for synthesis of 1-hydroxy-2-naphthaldehyde phosphorylated on a carbon atom in the second aromatic chain.

Advantageously, one synthesis method in accordance with the invention comprises a phosphorylation stage of a compound, dihydroxylated 2-naphthaldehyde, hydroxylated on a carbon atom 1 in the first aromatic chain and one of the carbon atoms in the second aromatic chain, said phosphorylation corresponding to substitution of the hydroxyl group in the second aromatic chain by a phosphate group.

Advantageously and in accordance with the invention, the phosphorylation stage is initiated by the phosphite, pyridine and iode technique, in a solution of $CH_2Cl_2$/THF (Stowel J. K. et al., 1995, Tetrahedron Lett., 36:182-185; Ladame S. et al., 2001, Phosphorous, Sulfur and Silicon, 174:37-47).

Advantageously and in accordance with the invention, the 1,6-dihydroxy-2-naphthaldehyde is phosphorylated, to end up, after deprotection (Page P. et al., 1999, Bioor. Med. Chem. 7:1403-1402), as 5-formyl-6-hydroxy-2-naphthylphosphate (FHN-P).

The invention also contemplates an aromatic aldolase-inhibitor compound, a method for aldolase and glycolysis inhibition, as well as a medicament, characterized in combination by any or all of the abovementioned or belowmentioned characteristics.

DETAILED DESCRIPTION.

Other objectives, characteristics and advantages of the invention can be seen in reading the following examples. FIGS. 1 to 5 illustrate the results obtained from these examples.

Synthesis and Physical-Chemical Analysis Methods

Every humidity-sensitive reaction was carried out in an argon atmosphere under anhydrous conditions.

Tetrahydrofurane (THF) and ethyl ether are distilled on sodium and benzophenone. Dichloromethane is distilled on $P_2O_5$. Pyridine and triethylamine are distilled on potassium. Methanol is distilled in the presence of a small amount of sodium. High-pressure liquid chromatography (HPLC) solvents are used without further purification.

The changing reactions were observed by thin-layer chromatography (TLC) on a silica plate (Merck 60-F254) using the appropriate eluent systems. Products were developed by UV radiation ($\lambda$=254 nm and 366 nm), by using iode vapor or a specific developer such as zinzade reagent (ammonium molybdate) for phosphorylated products, or Pancaldi's developer containing 5% cerium sulfate (IV), and an aqueous solution of sulfuric acid with 6% and 8% ammonium molybdate.

The products were purified by flash chromatography on silica gel (Merck-60, 230-400 mesh) or by high-pressure liquid chromatography (HPLC) prepared on a C18 reverse-phase column (Macherey-Nagel polygoprep C18, 12-25 $\lambda$m, 60A), with the appropriate eluent systems.

The RMN $^1$H, $^{13}$C and $^{31}$P spectra are recorded on the Bruker AC 200 or AC 250 spectrometers. Chemical shifts ($\delta$) are expressed in ppm, based on tetramethylsilane for the $^1$H and 13C nuclei, and based on phosphoric acid for the $^{31}$P nucleus. Coupling constant values are expressed in Hz. The following abbreviations are used: s—singlet; ws—widened singlet; d—doublet; t—triplet; q—quadruplet; and m—multiplet Mass spectra (DCI) were obtained using a Nermag R10-10 quadripolar spectrometer.

Elementary analyses were performed using an Eager 200 evaluator.

EXAMPLE 1

Synthesis of 5-formyl-6-hydroxy-2-naphthylphosphate (FHN-P)

The previously synthesized 1,6-dihydroxy-2-naphthaldehyde (0.21 g; 1.1 mmol) (Johnson W. S. J. and Shelberg W. E., 1945, J. Am. Chem. Soc., 67-1745-1753; Johnson W. S. J. et al., 1944, J. Am. Chem. Soc., 66:218-222; Bilger C. et al., 1987, Eur. J. Med. Chem. 22:363-365) is placed in solution in $CH_2Cl_2$ (34 mL). Anhydrous pyridine (0.1 g; 1.2 mmol) is added, maintained at 0° C. A mixture of iode (0.1 g; 1.2 mmol) and triethyl phosphite (0.23 mL; 1.32 mmol.) is then added, dissolved in $CH_2Cl_2$ (10 mL). The entire mixture is stirred at 0° C. for 1 hour, then left at room temperature. Water (20 mL) is added. The organic phase is washed with brine (NaCl—saturated water solution), then dried on $MgSO_4$. The solvent is eliminated under reduced pressure. After flash chromatography ($CH_2Cl_2$) a yellow oil is obtained (0.11 g; 31%): 1-hydroxy-2-naphthaldehyde-6-diethylphosphate.

Bromotrimethylsilane (0.15 µL; 1.1 mmol) is added slowly while stirring to the previously obtained 1-hydroxy-2-naphthaldehyde-6-diethylphosphate solution (0.054 g; 0.17 mmol), in solution in the anhydrous $CH_2Cl_2$ (200 µl) under nitrogen atmosphere. The resultant mixture is stirred for 3 hours at room temperature. Next, $Et_2O$/$H_2O$ (10:1) is added and the resultant organic phase washed with water. The pH of the aqueous phase is adjusted to 7.6 using 1 M sodium. The solution is lyophilized, ending up with 5-formyl-6-hydroxy-2-naphthylphosphate (FHN-P) as a white powder (0.050 g; 96%) in the form of sodium salt.

$^1$H NMR (250 MHz, $D_2O$): $\delta$7.11 (d, $^3J_{H3-H4}$=8.50 Hz, 1H, H3); 7.34 (d, $^3J_{H7-H8}$=8.00 Hz, 1H, H7); 7.41 (ws, 1H, H5); 8.24 (d, $^3J_{H4-H3}$=8.50 Hz, 1H, H4); 9.84 (d, $^3J_{H8-H7}$=8.00 Hz, 1H, H8); 9.91 (s, 1H, CHO).

$^{13}$C (50 HMz, $D_2O$): $\delta$114.73 (CS2); 116.93 (C10): 118.32 (d, $^3J_{C-P}$=3.57 Hz, C5); 120.13 (C8); 123.36 (d, $^3J_{C-P}$=5.00 Hz, C7); 123.42 (C9): 126.72 (C3);

128.31 (C4); 142.35 (C1); 158.49 (d, $^2J_{C-P}$=6.00 Hz, C6); 198.32 (CHO).

$^{31}$P NMR (81 MHz, $D_2O$): $\delta$0.56.

Mass spectrometry (FAB): 267, $\lambda_{max}{}^{H_2O}$ (pH 7.6): 392 nm ($\epsilon$5100 $M^{-1}.cm^{-1}$), 277 nm ($\epsilon$4650 $M^{-1}.cm^{-1}$).

EXAMPLE 2

Inhibiting Activity of Rabbit Muscle (RM) by FHN-P

Analysis Method:

Aldolase activity was measured using a coupled enzyme test system: the triose-phosphate isomerase and glycerol-3-phosphate deshydrogenase (TIM/GDH) system, following oxidation of the NADH (Boehringer-Mannheim, France) at 340 nm, by means of a SAFAS spectrophotometer preheated to 25° C. Testing began with the addition of the substrate (Fru(1.6)$P_2$; 1 nM in final concentration), to complete an aldolase solution created in a triethanolamine buffer (TEA buffer) (100 Mm TEA/HCl; 50 mM NaCl; 1 mM EDTA, pH 7.6; ionic strength 0.15), 0.42 mM of NADH, and containing both enzyme systems (10 µg/mL of GDH and 1 µg/mL of TIM) for a final volume of 1 mL. The construction, overexpression and purification of recombinant aldolase were carried out in accordance with Morris A. J. et al., 1993 (J. Biol. Chem., 265:1095-1100) and Berthiaume L. et al., 1993 (J. Biol. Chem., 268:10826-10835).

The substrate cleavage rate was determined by measuring the decrease in absorbance/minute at 340 nm. The aldolase was dialyzed overnight at 4° C. against a TEA buffer prior to use. The protein concentration was determined by spectrophotometry, using $\epsilon_{280}=0.91$ mL.mg$^{-1}$.cm$^{-1}$ as an extinction coefficient. Subunit concentration was determined on the basis of a molecular weight of 159,000 for an aldolase tetramer.

Figure 1:
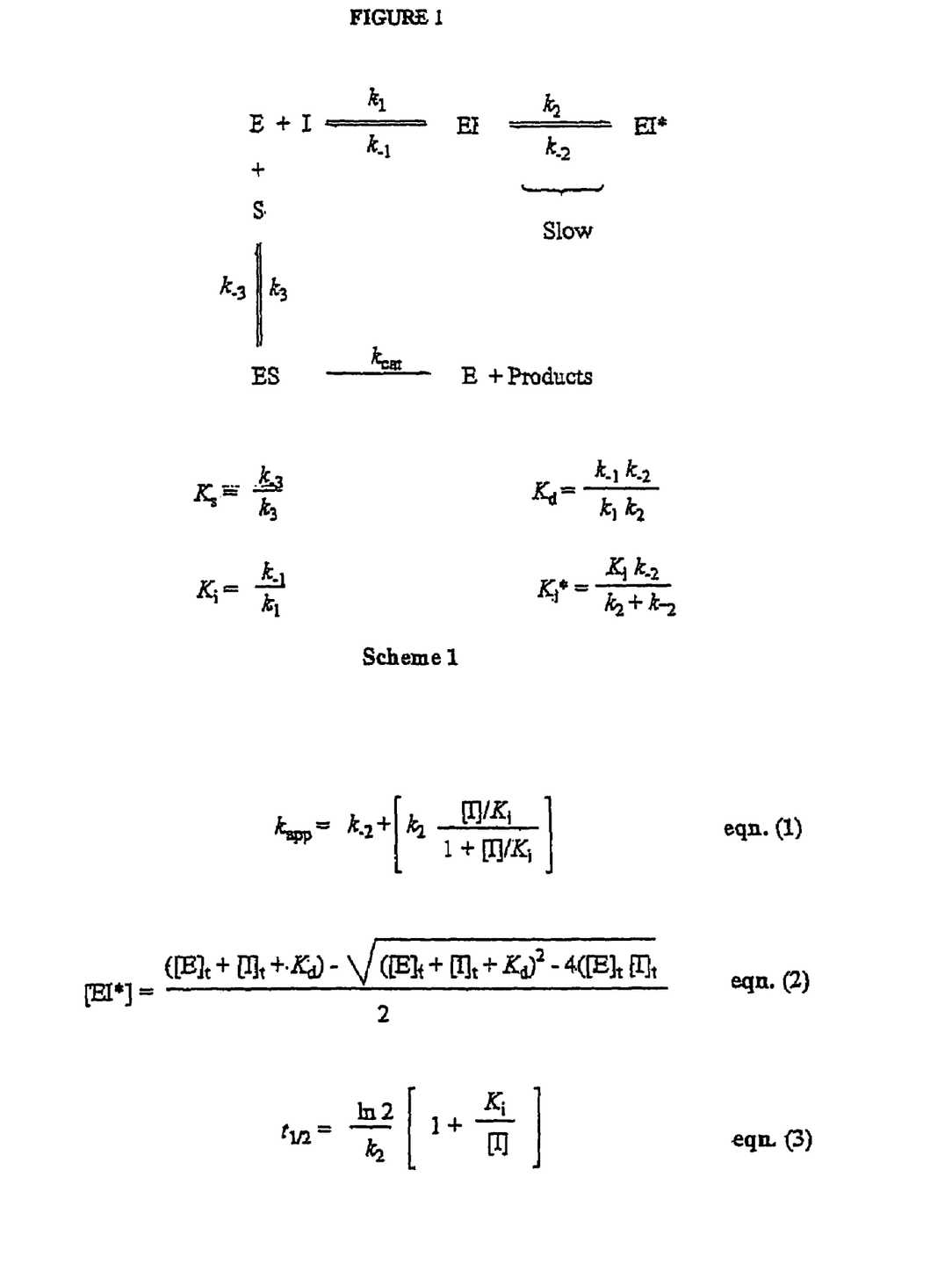
FIGS. 1 to 5 illustrate the results obtained from these examples.

Kinetic Method:

In the present case, reversible time-dependent inhibition (slow-binding inhibition) involves rapidly achieving equilibrium between the enzyme E and the inhibitor I, followed by an initial and kinetically more stable complex EI*, as shown in the reaction layout and reaction equations in FIG. 1, where $K_i^*$ represents the global inhibition constant, $K_i$ the Michaelis complex EI dissociation constant, rapidly formed, and $K_d$, the EI* complex dissociation constant.

Characterizing the Reversible Slow-Binding Inhibition:

When there is no substrate, the apparent first-order rate constant ($k_{app}$) describing the formation of the EI* complex is defined by the equation eqn.(1) (FIG. 1) (Morrison and Walsh, 1988, Adv. Enzymol. Relat Aeras Mol. Biol., 61:201-300).

The value of $k_{app}$ reflects the saturation kinetics whenever the inhibitor constant [I] increases, and varies between lower and upper limits of $k_{-2}$ and $k_2+k_{-2}$, respectively.

Upon reaching equilibrium, when [EI*]>[EI], the equation eqn.(2) (FIG. 1) is used, where $[E]_t$ and $[I]_t$ represent the initial concentrations of the enzyme and inhibitor, respectively, and $K_d$ is the EI* complex dissociation constant (Segal I. H., 1975, Enzyme kinetics: Behavior and Analysis of Steady-State and Rapid Equilibrium Enzyme Systems, Wiley-Interscience, New York).

In the extreme situation where $k_{-2}$ approaches zero, a reversible slow-binding inhibitor may resemble an irreversible one directed toward the active site. In this situation, the equation eqn.(3) is used for this type of inhibition (Meloche H. P., 1967, Biochemistry, 6:2273-2280). The semi-inactivation time of the enzyme ($t_{1/2}$) is defined as a function of the mutual inhibitor concentration and is graphically represented by a straight line crossing the Y-axis at $\ln(2/k_2)$ and crossing the X-axis at $-1/K_i$.

Experimental Protocol:

Native aldolase (5 µM of subunits) is incubated in the presence of FHN-P (0.05-1 mM) in TEA buffer. Enzyme activity is analyzed as a function of time using 10 µl aliquot portions.

Inactivation kinetics follow pseudo-first-order kinetics, and kinetic parameters $K_i$ and $k_2$ are determined by using the equation eqn.(3). To determine the reactivation rate, aldolase (25 µM of subunits in the TEA buffer) is incubated with 500 µM of FHN-P until reaching 90% inactivation. Excess inhibitor is removed by ultrafiltration with a PM-30 Millipore membrane. The enzyme-inhibitor complex is incubated in the TEA buffer (15 µM of subunits at final concentration) containing hexitol-P$_2$ (10 mM). Aliquot portions (10 µl) are removed at different times to measure aldolase activity.

Controls involve repeating the protocol without FHN-P. The reactivation process is analyzed as if it were a first-order reaction.

Monitored by UV-Visible Differential Spectroscopy.

Absorption spectra are measured using a Cary 1E Varian spectrophotometer at 25° C. The same TEA buffer is used for titrations and activity analyses. Absorption spectra are measured by two different methods, in particular as described in Gefflaut T. et al., 1986 (Bioorg. Med. Chem., 4:2043-2054) and Blonski C. et al., 1997 (Biochem J. 323:71-77).

For method A, absorption spectra are recorded as a function of time, between 250 and 500 nm, or at wavelengths corresponding to maximum or minimum absorption. Measurements are begun by adding FHN-P at varying final concentrations (0.1-1 mM) in the TEA buffer containing a fixed concentration of aldolase (10 µM of subunits). Measured absorption spectra for the enzyme complex are corrected using the absorbance of the buffer, the FHN—P, and the enzyme (measured separately). The differential absorption spectra thus obtained are used to calculate the value of the constants that define the formation of the aldolase-inhibitor complex.

Method B is used to titrate FHN-P by aminocaproic acid. For each analysis of TEA buffer containing a fixed concentration of FHN-P (10 µM), aminocaproic acid is added to obtain varying final concentrations (0.01-0.2 M). The differential absorption spectra, corresponding to the formation of a Schiff base, are recorded at different time intervals, then corrected with absorbance of the buffer, the aminocaproic acid and FHN-P (measured separately).

The apparent first-order rate constant ($k_{app}$) and the maximum threshold variations of absorption ($\Delta A_{max}$) are obtained for each test by applying the slow-binding absorption data to the first-order kinetic equation (or to both first-order kinetic mechanisms). The dissociation constant ($K_d$) for the Schiff base formed between the FHN-P and the aminocaproic acid is obtained from the absorption differences calculated at equilibrium by using the equation eqn.(2). The value of the dissociation constant ($K_i$) for the rapidly formed EI complex and that of the constant $k_2$ correspond to the slow formation of the EI* complex resulting from analysis of the values of the first-order constants based on the equations eqn.(1) or eqn. (3).

Every UV-visible differential test spectroscopy test using mutated aldolases (10 µM of subunits) is carried out using method A.

Monitored by Electrospray Ionization Mass Spectrometry (ESI-MS).

Electrospray ionization mass spectra are obtained in positive mode on a Finnigan TSQ 700 Mat Quadripole. The aldolases (50 µM of subunits in the TEA buffer) are incubated with 50 µM of FHN-P until reaching 60±5% inactivation. Excessive inhibitor is eliminated by ultrafiltration with an ammonium acetate buffer (10 mM, pH 5.5). Samples are prepared at around 10 pmol/µl in water/methanol (1:1, v/v) with a final concentration of 1 mM of ammonium acetate and 0.5% acetic acid. Samples are infused inside the spectrometer source with a continuous flow of 4 µl/min.

Results

Reversible Time-Dependent Inhibition of Aldolase by FHN-P.

Incubation of rabbit muscle aldolase with FHN-P leads to a loss of enzyme activity based on first-order kinetics.

The substrate Fru(1,6)P$_2$ and the analogue substrate hexitol-P$_2$, a powerful aldolase competitive inhibitor, shields the enzyme from inactivation by FHN-P (Table 1), corresponding to inhibition occurring at the enzyme active site.

The experimental conditions and measurements carried out, as seen in Table 1 below, are as follows: native aldolase from rabbit muscle (RM) (0.2 mg/mL) is incubated in the presence of a fixed concentration of FHN-P (250 µM) in the TEA buffer (final volume 1 mL; pH 7.6), with or without Fru(1,6)$P_2$ (1 mM); the enzyme activity of the aliquot portions is analyzed after incubating for 80 minutes.

By comparison, under the same experimental conditions as described in Table 1, the non-phosphorylated analogue of FHN-P (1,6-dihydroxy-2-naphthaldehyde, or DHNA, at 250 µM) is totally inactive, thus strongly suggesting that the phosphate group is functionally involved in attachment of FHN-P to the active site of the enzyme. The kinetic parameters are derived from the apparent first-order constants ($k_{app}$) measured for varying inhibitor concentrations (0.01-1.5 mM) based on the equation eqn.(3) and are displayed in Table 2.

TABLE 1

| Conditions | Specific activity (Unit/mg) |
|---|---|
| RM alone | 12.5 ± 0.5 |
| RM + FHN-P | 2.8 ± 0.3 |
| RM + FHN-P + Fru(1,6)$P_2$ | 5.2 ± 0.4 |
| RM + FHN-P + hexitol-$P_2$ | 9.9 ± 0.5 |
| RM + DHNA | 12.5 ± 0.5 |

TABLE 2

| Parameters | Value |
|---|---|
| $K_i$ (µM) | 250 ± 100 |
| $k_2$ (min$^{-1}$) | 0.07 ± 0.01 |
| $k_{-2}$ (min$^{-1}$) | 13 ± 7.10$^{-6}$ |
| $K_i$ (nM) | 40 ± 20 |

Enzyme activity is partly recovered by incubating the inactivated enzymes in a FHN-P-free solution containing a saturating concentration of hexitol-$P_2$ (10 mM). The value of the first-order constant ($k_{-2}$=1.3±7.10$^{-5}$ min$^{-1}$) reflecting recovery of enzyme activity is approximately four orders lower than the inactivation constant $k_2$.

Thus FHN-P behaves as a reversible slow-binding inhibitor. Based on the values displayed in Table 2, the global dissociation constant $K_i^*$ can be estimated at 40±20 nM. Moreover, enzyme activity cannot be restored following treatment of the enzyme-inhibitor complex by sodium borohydride, which suggests that the mechanism of inhibition by FHN-P leads to formation of a Schiff base with a lysine residue from the active site.

Interaction of FHN-P with Aminocaproic Acid

Figure 2:
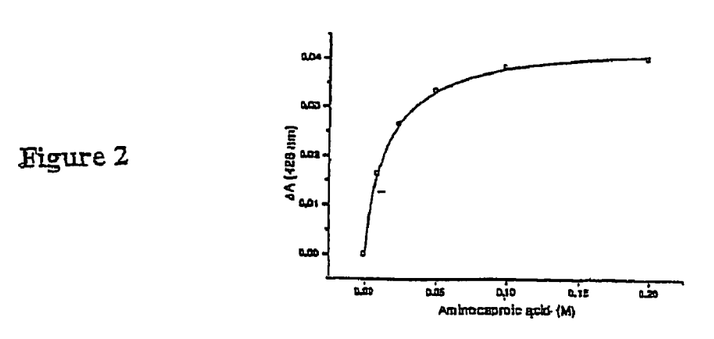

The FHN-P and the ε-amino group of aldolase lysine residues were taken as the model for formation of the Schiff base, with the reaction of FHN-P (10 µM) with aminocaproic acid (0.1-1 mM) as a reference, and which was monitored by UV-visible differential spectroscopy. The model reaction, represented in FIG. 3 (top), is characterized by changes in differential UV-visible absorbance corresponding to two maximums at 425 nm (Δε 3740±200 M$^{-1}$.cm$^{-1}$) and at 291 nm (Δε 13080±700 M$^{-1}$.cm$^{-1}$), which can be attributed to the formation of a Schiff base. This model reaction can also be characterized by two minimums at 367 nm (Δε−740±50 M$^{-1}$.cm$^{-1}$), and at 267 nm (Δε−5650±300 M$^{-1}$.cm$^{-1}$), resulting from loss of FHN-P inside the covalent complex. The present of isosbestic points at 388, 343 and 276 nm indicates that the intermediates are not cumulative and there is no longer a secondary reaction. Changes in differential absorbance for equilibrium become saturating whenever aminocaproic acid concentrations are increased (FIG. 2) and the reaction kinetics for each of these concentrations resemble that of a pseudo-first-order reaction mechanism and corresponds to a second-order constant, $k_{2nd}$ of 0.12±0.01 M$^{-1}$.min$^{-1}$ at 25° C. The value of the dissociation constant, $K_d$, of the FHN-P-aminocaproic acid is 16±3 mM (FIG. 2).

Interaction Between FHN-P and Rabbit Muscle Aldolase

Figure 3:
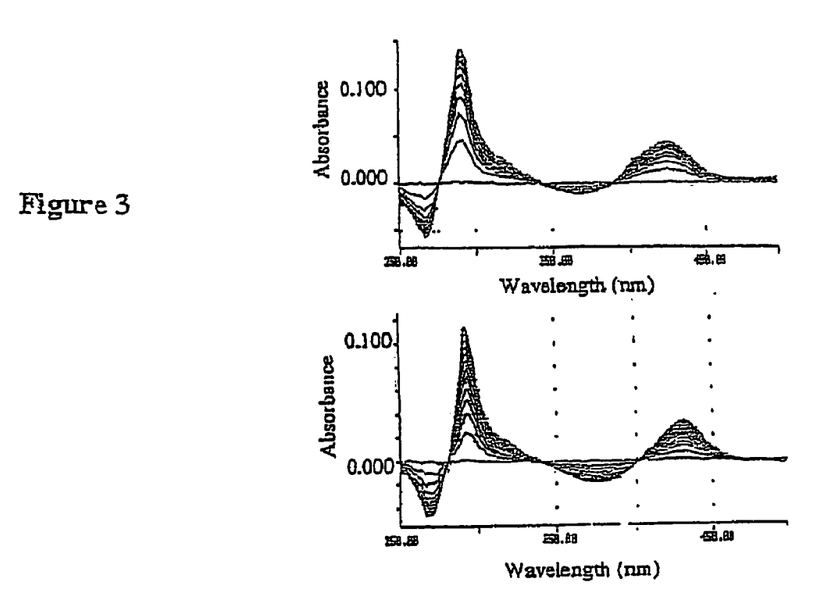

When FHN-P (final concentration of 0.1-1 mM) is added to a solution containing native aldolase (10 µM of subunits), the resultant UV-visible differential spectrum shows maximums of 431 and 293 nm, minimums of 376 and 268 nm, and isosbestic points of 401 and 279 nm (FIG. 3, bottom). The slight differences in band positions with the reaction model may be attributed to differences in the FHN-P protein environment in comparison to the model system. The changing spectra of absorbance differences coincides with two distinct first-order mechanisms. The rapid kinetics phase can be seen in a more significant change in absorbance and saturating behavior at a high inhibitor concentration, correlated with a total loss of enzyme activity. A slow kinetics phase can also be seen when the analyses are carried out at saturating concentrations of hexitol-$P_2$ (10 mM). This slow kinetics phase, which corresponds to a constant thirty times weaker and which contributes to one-fourth of the final absorbance variation is not linked to the inhibition observed. At these saturating concentrations, the molar absorption coefficients relative to the linked FHN-P are calculated assuming that the for active aldolase sites are occupied: $\Delta\epsilon_{431}$=3600±200 M$^{-1}$.cm$^{-1}$; $\Delta\epsilon_{376}$=−2140±110 M$^{-1}$.cm$^{-1}$; $\Delta\epsilon_{293}$=12480±650 M$^{-1}$.cm$^{-1}$; and $\Delta\epsilon_{268}$=5080±250 M$^{-1}$.cm$^{-1}$.

Stoichiometry of the FHN-P link to aldolase for maximum inhibition is consistent with the differential molecular absorbances arising from the aminocaproic acid-FHN-P complex, which foreshadows the EI* complex with 3.9-4.2 mols of FHN-P linked per tetrameric aldolase mole.

Figure 4:
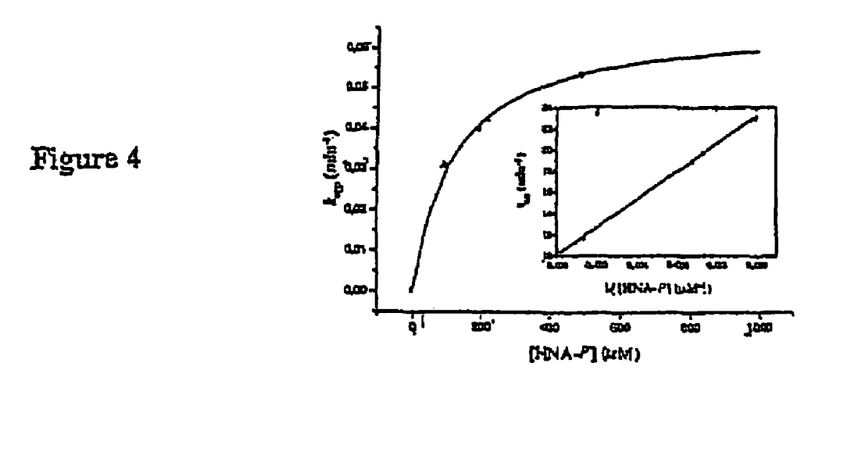

The kinetic parameters $K_i$ and $k_2$ characterizing the formation of the EI* complex are determined on the basis of data set forth in FIG. 4 in accordance with the equations eqn.(1) or eqn.(3) and which result in the values $K_i$=125±25 µM, $k_2$=0.067±0.004 min$^{-1}$ and $t_{1/2}$~6 min.

The global inhibition constant $K_i^*$, calculated on the basis of these latter results, corresponds to 25±15 nM.

Analysis of the Aldolase-FHN-P Complex by Electrospray Ionization Mass Spectrometry.

Figure 5:
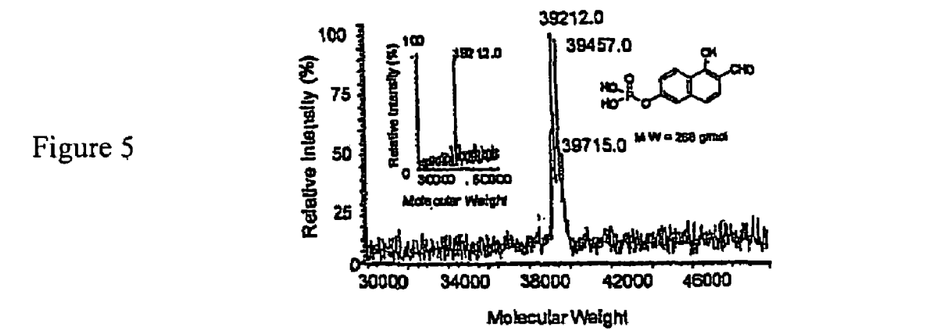

Analysis of an aldolase-FHN-P complex by electrospray ionization mass spectrometry resulted in molecular masses as follows: an aldolase monomer (39212 Da); a binary complex between an aldolase subunit and the FHN-P (39460 Da), in the form of a Schiff base, and traces of a tertiary complex between an aldolase subunit and 2 molecules of FHN-P (39712 Da) (FIG. 5).

Interaction Between Mutant RM Aldolases and FHN-P.

Residues of lysine 106, 146 and 229 residues are located at the active aldolase sites and thus are candidates for causing inactivation by forming a Schiff base with the FHN-P. In order to identify which lysine is responsible for the differential absorbances in the presence of FHN-P, sporadic mutations of these lysine residues were created and named: K107M (Research Collaboratory for Structural Bioinformatics Protein Databank), K146M (Blonski C. et al., 1997, Biochem. J. 323:71-77) and K2299M (Research Collaboratory for Structural Bioinformatics Protein Databank). Comparison of the atomic coordinates for K107M, K229M and the native enzyme show that these structural mutations are isomorphic in comparison to the wild-type enzyme (standard deviations ("rms deviations") of atomic coordinates in comparison to native aldolase are 0.41 Å and 0.48 Å, respectively, for the K107M and K229M structures). UV-visible differential spectroscopy (method A) was used to examine formation of the enzyme complex for each sporadic mutation in the presence of a fixed concentration of FHN-P (300 µM). Analysis of data obtained at 431 nm is displayed in Table 3.

TABLE 3

| Aldolase | Specific activity (units/mg) | Residual specific activity (%) | $k_{app}$ ($min^{-1}$) | ΔA relative to 432 nm (%) |
|---|---|---|---|---|
| Wild-type | 12.5 | ud (undetected) | 0.045 ± 0.0025 | 100 |
|  |  |  | 0.0015 ± 0.00035 | 25 |
| K229M | $3 \cdot 10^{-6}$ | ud | 0.040 ± 0.0025 | 95 |
|  |  |  | 0.0015 ± 0.0003 | 25 |
| K107M | 0.7 | 95 | 0.0015 ± 0.0005 | 30 |
| K146M | $2 \cdot 10^{-3}$ | ud | 0.005 ± 0.0005 | 98 |
|  |  |  | 0.0015 ± 0.0003 | 25 |

Differential spectra observed for the K229M mutation are identical to those observed with wild-type aldolase. Changes in reaction can be justified by two distinct first-order mechanisms. The kinetic parameters and the level of the EI* complex formed are identical to those obtained with the wild-type enzyme, with Lys-229 being excluded as a lysine residue directly responsible for formation of the Schiff base.

By comparison, differential spectra for the K107M mutation and FHN-P demonstrate a slow kinetics phase whose constant and maximum absorbance are identical to the values of the slow phase observed for the wild-type enzyme. The absence of the rapid phase added to the absence of enzyme inhibition is proof that Lys-107 is involved in the reversible time-dependent inhibition.

Reaction of the K146M mutation with FHN-P results in a global change to absorbance at equilibrium, comparable to what was observed for wild-type aldolase (Table 3). The kinetics phase associated with enzyme inhibition, albeit corresponding to a first-order mechanism, differs from that observed in the case of wild-type aldolase by a very slow formation of Schiff base. Substitution of the Lys-147 by a methionine therefore produces a significant drop in the rate of EI* complexes formed, though it does not hamper the ability of the mutation to form the complex. Accordingly, the Lys-146 is not required to form the Schiff base, though it does facilitate it considerably.

The invention claimed is:

1. An aromatic compound comprising an aldehyde group, a phenol group and a phosphate group or a mimetic thereof, wherein:
   its aromatic nucleus comprises two aromatic benzene chains,
   it corresponds to the following general formula:

(I)

where:
   The aldehyde group (—CHO) and the phenol group (—OH) are linked to two adjacent carbon atoms from the same aromatic chain, known as the first aromatic chain,
   and linked to a carbon atom in a second aromatic chain, known as the second aromatic chain, with R a phosphate group or a phosphate group mimetic selected from among:
   a enzymolabile protecting group adapted to allow said aromatic compound to pass through the cell and/or parasite membrane systems passively, and to be able to generate, once inside a cell or parasite, the formation of a phosphate group or a stable phosphate group analogue
   a stable phosphate group analogue adapted to preserve the aromatic compound of spontaneous or enzyme dephosphorylation.

2. The aromatic compound of claim 1, wherein it has the general formula:

(II)

where $R_1$ is a phosphate group or a phosphate group mimetic.

3. The aromatic compound of for any one of claims 1 and 2, wherein the enzymolabile protecting group is a group tending to be deprotected by one or more intracellular esterases.

4. The aromatic compound of claim 3, wherein the enzymolabile protecting group presents the following general formula:

(III)

where R' is selected from among one of the following groups:

(IV)

(V)

5. The aromatic compound of claim 3, wherein the enzymolabile protecting group presents the following general formula:

(VI)

where R" is selected from among one of the following groups:

(VII)
(VIII)
(IX)
(X)

6. The aromatic compound of claim 3, wherein the enzymolabile protecting group presents the following general formula:

(XI)

where R'" is selected from among one of the following groups:

(XII)

7. The aromatic compound of any one of claims 1 and 2, wherein the stable phosphate analogue is selected from among one of the following groups:
methylenephosphonate
difluoromethylenephosphonate
monofluoromethylenephosphonate 8. The aromatic compound of any one of claims 1-5 or 6, wherein a hydrogen atom from at least one carbon atom from at least one of the aromatic chains is substituted by a substituent, said hydrophobic substituent adapted to improve the global hydrophobicity of the aromatic compound.

9. The aromatic compound of claim 8, wherein the hydrophobic substituent(s) is(are) one of the alkyl groups of the principal chain comprising a maximum of three carbon atoms.

10. A method for synthesizing a compound 1-hydroxy-2-naphthaldehyde phosphorylated on a carbon atom in the second aromatic chain, according to claim 1, wherein a phosphorylation stage of a dihydroxylated compound 2-naphthaldehyde is performed, hydroxylated on carbon atom 1 of the first aromatic chain and one of the carbon atoms in the second aromatic chain, said phosphorylation corresponding to substitution of the hydroxyl group in the second aromatic chain by a phosphate group.

11. A synthesis method according to claim 10, wherein phosphorylation is initiated by the triethyl, phosphite, pyridine and iode technique, in a solution of $CH_2Cl_2$/THF.

12. A synthesis method according to any one of claims 10 or 11, wherein phosphorylation is performed on 1,6-dihydroxy-2-naphthaldehyde to obtain 5-formyl-6-hydroxy-2-naphthylphosphate.

* * * * *